(12) United States Patent
Koehler et al.

(10) Patent No.: US 8,960,990 B2
(45) Date of Patent: Feb. 24, 2015

(54) MIXER WAVEFORM ANALYSIS FOR MONITORING AND CONTROLLING CONCRETE

(75) Inventors: Eric Koehler, Cincinnati, OH (US); Steve Verdino, Hamilton, OH (US); Robert Culley, West Chester, OH (US)

(73) Assignee: Verifi LLC, West Chester, OH (US)

( * ) Notice: Subject to any disclaimer, the term of this patent is extended or adjusted under 35 U.S.C. 154(b) by 192 days.

(21) Appl. No.: 13/260,391

(22) PCT Filed: Mar. 23, 2010

(86) PCT No.: PCT/US2010/028207
§ 371 (c)(1),
(2), (4) Date: Sep. 26, 2011

(87) PCT Pub. No.: WO2010/111204
PCT Pub. Date: Sep. 30, 2010

(65) Prior Publication Data
US 2012/0020180 A1    Jan. 26, 2012

Related U.S. Application Data

(60) Provisional application No. 61/164,174, filed on Mar. 27, 2009.

(51) Int. Cl.
| | | |
|---|---|---|
| B28C 5/18 | (2006.01) | |
| B28C 7/04 | (2006.01) | |
| G05B 21/00 | (2006.01) | |
| G05D 21/02 | (2006.01) | |
| B28C 7/02 | (2006.01) | |
| G01N 33/38 | (2006.01) | |

(52) U.S. Cl.
CPC ............... *G05D 21/02* (2013.01); *B28C 7/026* (2013.01); *G01N 33/383* (2013.01)
USPC ................. 366/61; 366/40; 366/60; 700/265

(58) Field of Classification Search
USPC .................................. 366/44, 60, 61; 700/265
See application file for complete search history.

(56) References Cited

U.S. PATENT DOCUMENTS

| | | | | |
|---|---|---|---|---|
| 2,618,472 | A | * | 11/1952 | Castendyck ..................... 366/44 |
| 4,008,093 | A | | 2/1977 | Kitsuda et al. |
| 5,713,663 | A | | 2/1998 | Zandberg et al. |
| 6,484,079 | B2 | | 11/2002 | Buckelew et al. |
| 6,611,755 | B1 | | 8/2003 | Coffee |
| 6,876,167 | B1 | | 4/2005 | Jones |
| 6,876,904 | B2 | * | 4/2005 | Oberg et al. .................. 700/265 |
| 7,048,430 | B2 | * | 5/2006 | Birmingham et al. .......... 366/57 |
| 8,020,431 | B2 | * | 9/2011 | Cooley et al. ................ 73/54.03 |
| 2002/0015354 | A1 | | 2/2002 | Buckelew et al. |
| 2004/0176876 | A1 | * | 9/2004 | Oberg et al. .................. 700/265 |
| 2005/0159843 | A1 | * | 7/2005 | Oberg et al. .................. 700/265 |
| 2007/0185636 | A1 | | 8/2007 | Cooley et al. |
| 2008/0316856 | A1 | * | 12/2008 | Cooley et al. ................. 366/142 |
| 2009/0037026 | A1 | | 2/2009 | Sostaric et al. |
| 2011/0029134 | A1 | | 2/2011 | Hazrati et al. |
| 2012/0016523 | A1 | * | 1/2012 | Koehler et al. ............... 700/265 |

FOREIGN PATENT DOCUMENTS

EP    0126573    11/1984

OTHER PUBLICATIONS

Young, Form PCT/ISA/210, International Search Report for International Patent Application No. PCT/US2010/028207, May 4, 2010, 3 pages.

Young, Form PCT/ISA/237, Written Opinion of the International Searching Authority for International Patent Application No. PCT/US2010/028207, May 4, 2010, 6 pages.

* cited by examiner

*Primary Examiner* — Walter D Griffin
*Assistant Examiner* — Abbas Rashid
(74) *Attorney, Agent, or Firm* — Craig K. Leon

(57) ABSTRACT

Method and system for motoring and obtaining information about quantity and characteristics of cementitious material In a rotating mixing drum. The present invention involves analysis of a sequence of values corresponding to a waveform reflecting the hydraulic pressure required to turn a concrete mixing drum at successive instances during rotation. Preferred embodiments involve the conversion of this time-domain data into the frequency-domain. Behavior of multiple harmonics can be examined in real time and further information obtained regarding physical properties of the concrete. Rheology or other properties can be adjusted by introducing a liquid into the concrete, based on a comparison between time-domain and/or frequency-domain values derived from a sample concrete in the drum and previously stored time-domain and/or frequency-domain values, which are preferably correlated with physical characteristics of concrete, such as slump, slump flow, load weight, and other factors.

19 Claims, 5 Drawing Sheets

MIXER WAVEFORM ANALYSIS FOR MONITORING AND CONTROLLING CONCRETE

CROSS-REFERENCE TO RELATED APPLICATION

This application is a 371 of PCT/US2010/028207 filed Mar. 23, 2010, which claims the benefit of U.S. Provisional Application No. 61/164,174 filed Mar. 27, 2009.

FIELD OF THE INVENTION

The present invention relates to manufacturing of concrete, and more particularly to a method for monitoring and obtaining information about the quantity and/or characteristics of cementitious material in a mixing drum by analyzing the energy waveform (e.g., hydraulic pressure), and, more preferably, converting the time-domain waveform into the frequency-domain spectrum whereby further information may be obtained and assessed.

BACKGROUND OF THE INVENTION

It is known to monitor and control the "slump," or fluidity property, of concrete in ready-mix delivery trucks by using sensors to monitor the energy required for rotating the mixing drum (e.g., U.S. Pat. No. 4,008,093) and/or the torque applied to the drum by hydraulic pressure (e.g., U.S. Pat. No. 5,713,633). The higher the amperage or hydraulic pressure needed to turn the drum at a given speed, the stiffer or less flow-able (lower slump) the concrete mixture.

Automated control systems enable transportation of concrete in mixer trucks over longer distances by allowing for adjustment of slump in transit through the addition of water or other liquids. A hydraulic sensor coupled to the hydraulic drive and/or a rotational speed sensor connected to the drum may be used for monitoring purposes. Such sensors can be wirelessly connected to a computer processing unit and a wireless communication system to permit modifications to be made during operation. See e.g., U.S. Ser. No. 10/599,130 (Publication No. 2007/01856A1).

The monitoring of concrete slump involves calibrating the outputs or values obtained from the hydraulic sensor and/or electrical sensor on a mixing truck, and correlating these with slump values obtained using a standard slump cone test. In the standard slump cone test, a 12-inch truncated cone containing fresh concrete is removed to permit the concrete to drop, and the vertical height drop of the concrete is measured (ASTM C143-05). Concrete having this known slump property is then added into a rotatable drum mixer so that a hydraulic or electrical value, obtained as an output from the sensor, can be stored into a memory location and subsequently correlated by a computer processing unit. During the delivery of the concrete to a customer, the concrete stiffens with time as a result of hydration, evaporation, and other factors, and the sensors detect this as increased hydraulic or electrical energy required for turning the mixing drum. The on-board computer processing unit compares the detected energy value obtained from the sensor or sensors and compares this to a value or value range stored in computer-accessible memory. If the sensors and computer processing unit (CPU) detect that the concrete is beginning to stiffen, the CPU can then be triggered to activate metering or pumping devices to inject water or other liquid (e.g., chemical dispersant) into the concrete to restore the slump to the desired value.

Other methods are available for manually measuring workability (which is defined as the ease and homogeneity with which the concrete can be mixed, placed, consolidated, and finished). For example, in the flow table test (EN 12350-5), concrete is filled into a cone that is placed on a moving table. The table consists of a flat plate that is hinged on one end, such that the other end can be lifted and dropped a fixed distance. After the cone is removed, the plate is lifted and dropped a certain number of times and the horizontal flow of the concrete is measured. For highly flowable concrete mixtures, such as self-consolidating concrete, the slump flow test is used (ASTM C 1611-05). In this test, concrete is placed in a standard slump cone, the cone is removed, and the horizontal spread—rather than the vertical drop—is measured.

The present inventors believe that a major problem of current slump monitoring information is that such equipment provides only information about slump. Additional information about the quantity and properties of the concrete in the drum, as well as the characteristics of the drum itself should be known in order to monitor and control the properties of the concrete more completely and effectively.

The present inventors also believe that a major problem of current slump monitoring equipment is determining when mixing of components to produce a uniform mix is completed. When ingredients are initially added to a mixer, the energy to rotate the drum increases as the ingredients are combined and then decreases as mixing progresses and the concrete becomes more fluid. In current practice, the number of drum revolutions is fixed to assure full mixing. If this number is greater than actually required to achieve full mixing, unnecessary energy and time are wasted. If this number is fewer than actually required to achieve full mixing, un-mixed material may be discharged from the drum prematurely. It would be desirable to have a method for monitoring the completion of mixing.

Hence, a novel method and system for monitoring and adjusting concrete rheological properties in mixing drums are needed.

SUMMARY OF THE INVENTION

The present invention provides a method and system for monitoring and controlling rheological properties and other characteristics of a cementitious material being mixed in a rotatable mixing drum. Whereas prior art methods analyzed a single hydraulic pressure—measured instantaneously or averaged from measurements over time—to compute slump or consistency, the present invention involves consideration and analysis of the variations in the measured energy (e.g., hydraulic pressure) in addition to the average energy to obtain further information about the cementitious material, such as extent of mixing, rotational drum speed, or amount of material. In further exemplary embodiments, this time-domain information is converted into the frequency-domain, such as by using Fast Fourier Transform (FFT), Discrete Fourier Transform (DFT), or variations thereof. By comparing waveform (time-domain) or converted waveform data (e.g., FFT) obtained from a given cementitious mix, and comparing to stored values, the quantity and characteristics of the material may be obtained and rheology and other properties can be adjusted such as through addition of liquids or other components.

Thus, an exemplary method of the present invention for mixing a cementitious material, comprises: providing a rotatable mixing drum having an inner drum wall and at least one mixing blade mounted on the inner drum wall, the mixing drum containing components for making a hydratable cementitious material; rotating said mixing drum at constant speed $S^{C1}$ in the range of 1-25 revolutions per minute; providing a sequence of values over time corresponding to the energy required to rotate the mixing drum, said sequence of values being monitored at a frequency of at least 10 times constant speed $S^{C1}$; comparing the provided sequence of values with a sequence of values previously stored in data memory storage location; and adjusting rheology or other property of the cementitious material contained in said mixing drum by introducing a liquid or other cementitious material component into the mixing drum.

In preferred methods, it is the hydraulic pressure which is monitored over time, and the sequence of values obtained which correspond to the hydraulic pressure is stored in a computer-accessible data memory storage location, so that it can be displayed on a monitor or printed on paper, and also so that it can be compared with a previously stored sequence of values taken from a control cementitious sample.

In preferred methods and systems, the sequence of values, which can be plotted graphically in terms of energy (e.g., hydraulic pressure) in the time-domain, is converted into the frequency-domain using a Fast Fourier Transform (FFT) algorithm such that the data can be analyzed in terms of frequency components. Accordingly, the rheology of the cementitious material can be monitored based on previously stored FFT data. For example, if the data indicates that the cementitious material is stiffening, this could be quickly determined by measuring changes in peak amplitude and phase shift in the frequency-domain, such that the rheology or other property of the cementitious material can be quickly adjusted by introducing liquid (e.g., water, chemical admixture, or both) into the mixing drum.

Thus, a preferred method of the invention comprises: rotating a mixing drum containing a cementitious mixture at a constant speed in the range of 1-25 revolutions per minute; providing a sequence of time-domain values corresponding to the amount of energy required to rotate the mixing drum, converting the sequence of time-domain values into frequency-domain values, comparing the frequency-domain values to stored frequency-domain values; and introducing a liquid into the mixing drum, based on the compared values.

Values or electrical outputs from a sensor corresponding to the amount of electrical energy or more preferably corresponding to the amount of hydraulic pressure required to turn the drum can be stored into computer-accessible memory location, and can be displayed graphically as a periodic waveform. The sequence of energy values over time should be based on a sampling frequency of at least 10 times per revolution of the revolving mixing drum, or even more if greater accuracy is desired. Preferably, the mixing drum will have at least one or more internal mixing blades to enable the plotting of a periodic waveform having two or more peaks per period in the time-domain. Hence, in preferred embodiments of the invention, these waveform values can be converted into the frequency-domain, such as by conversion using Fast Fourier Transform (FFT) and/or discrete Fourier transform (DFT). Analysis of either time-domain or frequency-domain data or both can enable analysis of one or more physical cementitious material mixing parameters selected from the group consisting of (a) load weight, (b) load volume, (c) concrete density, (d) concrete air content, (e) concrete slump, (f) concrete slump flow, (g) concrete flow table value, (h) concrete rheology (e.g., yield stress, viscosity, thixotropy), (i) segregation of concrete components, (j) concrete setting, (k) inclination of the mixing drum, (l) size and configuration of the internal drum structure; and (m) build-up of concrete in the drum.

Additionally, analysis of the time-domain or frequency-domain data can be used in determining the progress of mixing.

For example, a liquid (e.g., water, chemical admixture, or both) can be introduced into the mixing drum based on an analysis of the frequency-domain data. Using a transformation algorithm such as FFT or discrete Fourier transform (DFT) is an efficient way of decomposing or otherwise converting a sequence of hydraulic energy values into components of different frequencies analyzed in the frequency-domain, such that one or more of the physical parameters of the concrete, as mentioned above, can be monitored, analyzed, and, if necessary, adjusted by introducing a liquid or other cementitious component into the mixing drum.

The invention also provides a mixing system that comprises: a mixing drum having an inner drum wall and at least one mixing blade mounted on said inner drum wall, said mixing drum containing components for making a hydratable cementitious material; a hydraulic pressure drive operative to rotate said mixing drum at constant speed $S^{C1}$ in the range of 1-25 revolutions per minute; a sensor operative to provide a sequence of values over time corresponding to the energy required to rotate the mixing drum; a computer processing unit for monitoring values provided by the hydraulic pressure sensor corresponding to the amount of hydraulic pressure required by the hydraulic drive; a data memory storage location for storing a first set of data corresponding to first sequence of values over time corresponding to the energy required to rotate the mixing drum containing a first hydratable cementitious material, said first sequence of values being monitored at a frequency of at least 10 times constant speed $S^{C1}$; said computer processing unit being further operative for receiving a second sequence of values over time corresponding to the energy required to rotate the mixing drum containing a second hydratable cementitious material, said second sequence of values being monitored at a frequency of at least 10 times constant speed $S^{C1}$; said computer processing unit being further operative for comparing said second sequence of values with said first sequence of values, and adjusting rheology or other property of said second hydratable cementitious material by introducing a liquid or other cementitious material component into said mixing drum based on said comparison. In preferred mixing systems, the computer processing unit is operative (a) to convert said first and second sequence of values, corresponding to corresponding to energy required to rotate the mixing drum containing cementitious material, into the frequency-domain; (b) to compare said first and second sequence of values after conversion into the frequency-domain, and (c) to adjust the rheology of cementitious material contained in said mixing drum by addition of liquid based on said comparison. Using either or both the time-domain or frequency-domain data, one or more properties of the cementitious material (e.g., slump, slump flow, load weight, air content, etc.) can be analyzed or modified such as by introducing liquid or other component into the cementitious material.

The method and system of the invention may be employed in stationary mixing drums, such as at a batching plant, or in delivery trucks having mixing drums. The analysis method may also be used in mixers other than drum mixers, such as single shaft mixers, double shaft mixers, and pan mixers. Further advantages and features of the invention may be described hereinafter.

BRIEF DESCRIPTION OF THE DRAWINGS

Further advantages and features of the present invention may be more readily comprehended when the following detailed description of preferred embodiments is taken in conjunction with the appended drawings wherein.

DETAILED DESCRIPTION OF EXEMPLARY EMBODIMENTS

Figure 1:
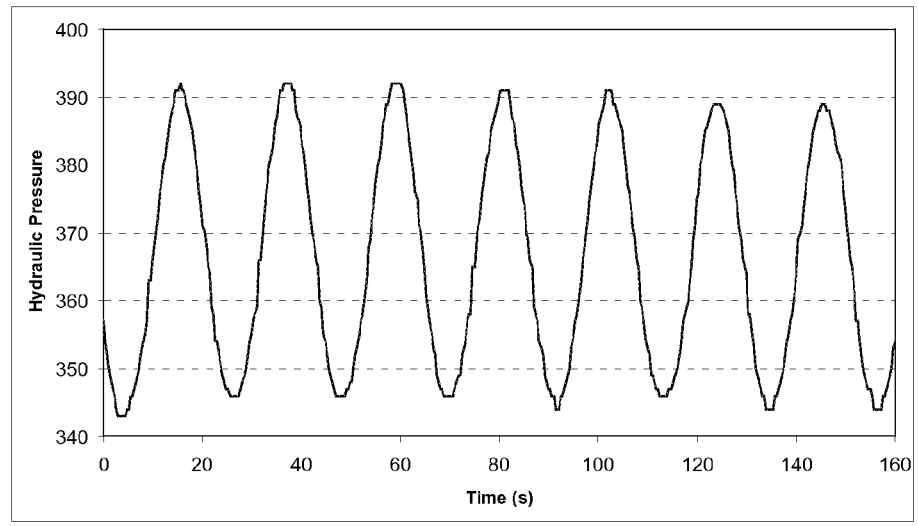
FIG. 1 is a graphic illustration of hydraulic pressure (i.e., energy as shown by waveforms) required to rotate an empty mixing drum.

The term "cementitious" as used herein refers to a material that comprises portland cement or portland cement substitutes which otherwise function as a binder to hold together fine aggregates (e.g., sand), coarse aggregates (e.g., crushed stone or gravel), or mixtures thereof.

Such cementitious materials may further include fly ash, granulated blast furnace slag, lime stone, or natural pozzolans, which may be combined with portland cement or be used to replace or substitute for a portion of the portland cement without serious diminishment of hydratable properties. Incidentally, a "mortar" refers to cement or cementitious mixture having a fine aggregate such as sand; while "concrete" refers more accurately to a mortar that also contains a coarse aggregate such as crushed stone or gravel. The use of the term "cementitious material" may be used interchangeably with the term "concrete," as concrete is most commonly provided by ready-mix trucks which have rotatable mixing drums, but the term "concrete" as used herein does not necessarily exclude the fact that the present invention can be used for delivering materials that contain only cement or cement substitutes (e.g., pozzolans) or mortars.

Cementitious materials deemed to be "hydratable" are those which harden by chemical interaction with water.

Cementitious materials may further contain chemical admixtures, such as water-reducing agents or high range water-reducing agents, viscosity modifying agents, corrosion-inhibitors, shrinkage reducing admixtures, set accelerators, set retarders, air entrainers, air detrainers, pigments, colorants, fibers for plastic shrinkage control or structural reinforcement, and the like.

Concrete delivery mixing trucks having slump control monitoring and control equipment, such as hydraulic and/or electric sensors for measuring the energy for turning the mixing drum, speed sensors for measuring the speed of rotation, temperature sensors for monitoring the atmospheric temperature as well as the mix temperature, and dispensing equipment, as well as the computer processing units for monitoring signals from the sensors and actuating the dispensing equipment are by now relatively well known in the industry. For example, such slump control systems, which can be used in association with wireless communication systems, are disclosed in U.S. Pat. No. 5,713,663; U.S. Pat. No. 6,484,079; U.S. Ser. No. 09/845,660 (Publication no. 2002/0015354A1); U.S. Ser. No. 10/599,130 (Publication no. 2007/01856A1); Ser. No. 11/764,832 (Publication no. 2008/0316856); and Ser. No. 11/834,002 (Publication no. 2009/0037026). A further exemplary system for monitoring and control using wireless communications in combination with sensors for monitoring various physical properties of the concrete mix is taught in U.S. Pat. No. 6,611,755 of Coffee. These teachings are incorporated herein by reference.

In view of the foregoing teachings, the present inventors believe that a number of exemplary embodiments of the invention may be practiced using conventional automated concrete mix monitoring equipment. Using automated slump-monitoring equipment available under the VERIFI® name from Grace Construction Products, Cambridge, Mass., and RS Solutions LLC, West Chester, Ohio, for example, one might, with slight modification of this commercially-available slump-monitoring equipment, perform the following steps: introducing into a rotatable mixing drum, having at least one and preferably two or more mixing blades mounted on the inner drum wall, a cementitious material; rotating the drum at constant speed $S^{C1}$ in the range of 1-25 revolutions per minute (rpm); providing a sequence of values corresponding to the energy (e.g., hydraulic pressure ("$P^H$")) over time required to rotate the drum, said sequence of values being monitored at a frequency of at least 10 times per drum revolution at constant speed $S^{C1}$; preferably storing these values in a first computer-accessible data memory storage location; comparing sequential measurements of $P^H$ at constant speed $S^{C1}$ over time with sequential measurements of $P^H$ at constant speed $S^{C1}$ as previously stored in another data memory storage location; and adjusting rheology or other property of the cementitious material by introducing a liquid into the mixing drum in response to this comparison.

In further exemplary methods and systems of the invention, the sequence of values, which can be plotted graphically in terms of energy (e.g., hydraulic pressure) over time in the time-domain, is converted into the frequency-domain using algorithms such as Fast Fourier Transform (FFT), Discrete Fourier Transform (DFT), or derivatives thereof, such that the data can be analyzed in terms of frequency components and the properties of the cementitious material can be monitored and/or adjusted based on the previously stored FFT data.

The present inventors believe that the use of FFT or Discrete Fourier Transform (DFT) or variations thereof can be used for transforming signals from the time domain into a frequency domain spectrum even though based on rotational data. For example, U.S. Pat. No. 6,876,168 B1 of Jones taught the speed of a rotating device, such as a DC motor, could be analyzed in the frequency domain by employing FFT or DFT to transform signals, generated by a sensor that measured dynamic characteristics of the DC motor. In the present case, however, a rotational speed sensor can be employed on the mixing drum itself, so that it is not necessary to use FFT or DFT to approximate rotational speed since this can be determined directly. Instead, by examining hydraulic pressure waveform data in the frequency-domain, the present inventors believe that complex sets of concrete mix and mixer characteristics, even against the dynamic effects of hydration and other factors, can be monitored, analyzed, and adjusted.

Slump-monitoring systems can be calibrated by measuring the slump of a sample concrete mix using standard slump cone method (e.g., measuring vertical drop height of concrete mix after removing cone and allowing sample to fall) and correlating the slump values with energy required to rotate the same concrete sample mix in the drum at a given speed for a given volume of mix material. This correlation can also be used for the purposes of the present invention, particularly where the hydraulic pressure values are analyzed in the frequency domain.

In further exemplary embodiments of the invention, monitoring of a sample concrete mix can be performed by measuring the slump flow of a concrete mix sample, and this is done by measuring the horizontal spread of the concrete sample mix after removing the slump cone and allowing the sample to spread on a surface. Hence, such slump flow values may also be correlated with the average energy (e.g., hydraulic pressure) to rotate the mixing drum at a given speed for a given volume of the sample concrete mix. The slump flow test is administered in accordance with ASTM C1611-05.

In still further exemplary embodiments of the invention, the present inventors believe that slump-monitoring systems can also be calibrated by using the flow table test (EN 12350-5) whereby concrete is filled into a cone that is placed on a moving table and the cone is removed so that the horizontal spread of the concrete sample can be measured, as described previously in the background. The flow table values obtained can then be correlated with average hydraulic pressure for a given speed for a given volume of mix material. This correlation can also be used for the purposes of the present invention, particularly where the hydraulic pressure values are analyzed in the frequency domain.

Hence, further exemplary mixing systems and methods of the invention comprise providing a sequence of values corresponding to average hydraulic pressure required to rotate the drum containing a known volume of a concrete mix at a given speed and volume, with values previously stored in a computer accessible memory location and corresponding to standard slump cone values (vertical drop test; See ASTM C143-05), slump flow values (horizontal spread' See ASTM C1611-05), and/or flow table values (See EN 12350-5) obtained from a concrete mix.

Figure 9:
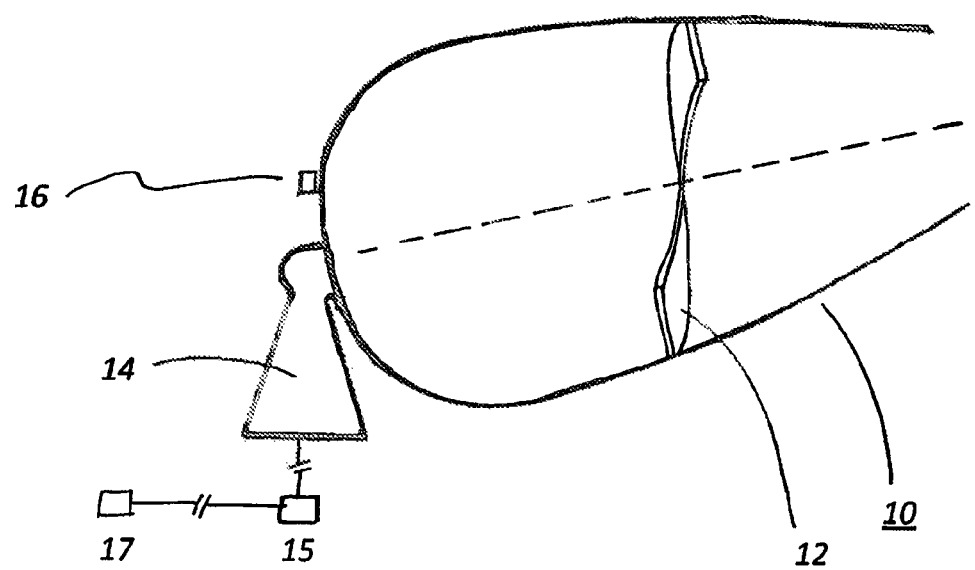
FIG. 9 is a diagrammatic representation of a PRIOR ART concrete mixing drum showing a partial view of a blade mounted on the inner wall of the drum, drive means for rotating the mixing drum and sensor for measuring energy required to rotate the drum, sensor for monitoring rotational speed of the mixing drum, computer processing unit for receiving signals from the sensors, and computer-accessible memory.

FIG. 9 illustrates a PRIOR ART concrete mixing drum 10 having at least one blade mounted on the inner drum wall (as designated at 12), drive means for rotating the mixing drum and sensor for monitoring the energy (both designated as at 14) required to rotate the mixing drum 10, a sensor 16 for monitoring the rotational speed of the drum 10 (wherein the dotted line shown in FIG. 9 depicts the rotational axis of the mixing drum 10). Such mixing drum configurations are known in the art (See e.g., U.S. Pat. No. 6,611,755 wherein a truck-mounted mixing drum is illustrated with drum rotation sensor 280 in FIG. 23 for monitoring speed of the drum). The speed sensor 16, drive means 14, and sensor 14 are electrically connected to or communicative with a computer processing unit 15 which is, in turn, electrically connected to or communicative with computer-accessible memory 17.

The present invention concerns a patentable improvement in processing methodology programmed into the computer-accessible memory (17).

FIG. 1 shows at typical time-domain energy waveform (hydraulic pressure) over time (seconds) required for turning an empty concrete mixing drum. These waveforms appear as a sequence of continuous sinusoidal curves. While hydraulic pressure is primarily mentioned herein, since most concrete delivery mixing trucks employ hydraulic pressure for turning the drum, references to hydraulic pressure should be understood to apply as well to or include electrical energy (e.g., current, voltage, or power readings) which is similarly oscillatory in nature, having amplitude varying with time.

Figure 2:
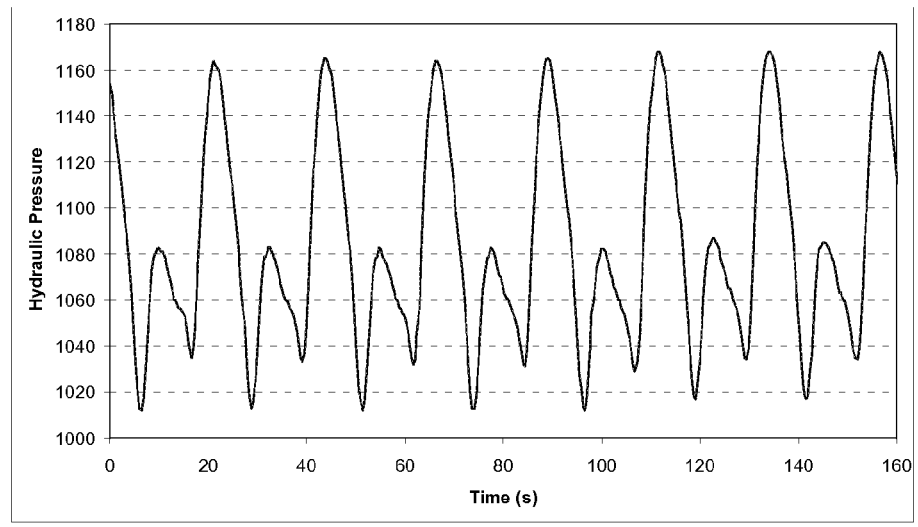
FIG. 2 is a graphic illustration of hydraulic pressure required to rotate a mixing drum loaded with concrete.

FIG. 2 shows a typical hydraulic pressure waveform for a rotating mixing drum loaded with a concrete mixture. The interior surface of the mixing drum contained two mixing blades attached to the interior surface of the drum and arranged in spiral fashion around the rotational axis of the drum. The present inventors believe that the number of blades, two in this case, and the characteristics of the empty drum are reflected by the pair of short and tall peaks plotted in the graph.

The hydraulic pressure waveform of a given concrete material having a relatively uniform consistency and a known slump or slump flow (such as determined by standard slump cone) and known quantity may be stored in computer-accessible memory as a sequence of values (from the output of a hydraulic pressure sensor) corresponding to the amount of hydraulic pressure required during the turning of the mixing drum at successive instances during rotation. After the mixing drum is emptied and the components of another concrete batch of the same design (same components and percentages thereof) are placed into the drum, the system can be programmed to recognize when the components (cement, water, aggregate materials) have been adequately mixed and can also determine how much of cementitious material is placed into the drum, and this can be done by analyzing variations in hydraulic pressure required to rotate the mixing drum over time. Hence, one may not need to compute average energy (which would otherwise require a number of drum rotations to be averaged out) but would presumably require fewer rotations to determine when uniform consistency has been reached in the given mix simply by ascertaining when the hydraulic pressure waveform matches or sufficiently approximates a control sample and stored in computer-accessible memory location. In addition, pattern recognition, as will be further discussed hereinafter, can be used to determine when a waveform corresponds to certain targets. The waveform could also be transferred to the frequency domain from the time domain.

Figure 3:
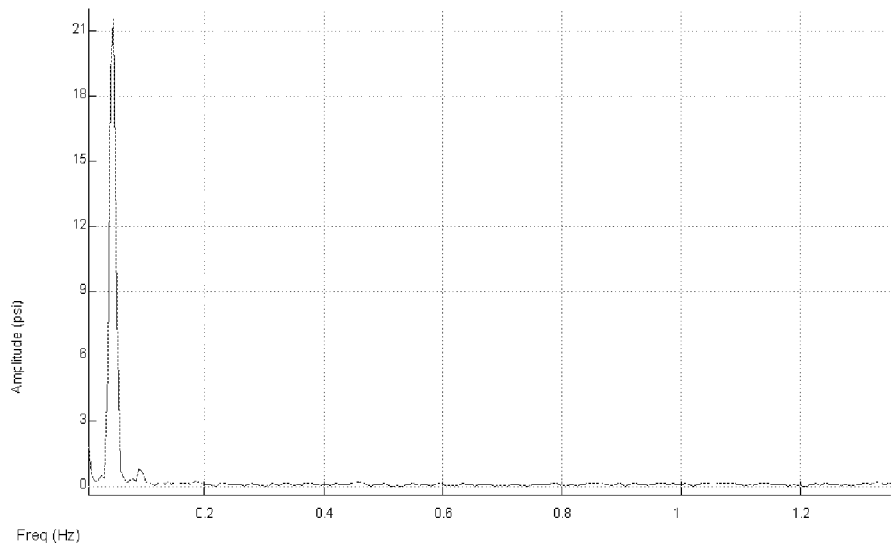
FIG. 3 is a graphic illustration of a frequency domain spectrum of an empty mixing drum of FIG. 1 computed from Fast Fourier Transform (FFT) analysis.

FIG. 3 illustrates hydraulic pressure energy in terms of Fast Fourier Transform (FFT) analysis of the empty drum pressure waveform. In other words, the sequence of energy readings is converted from the time-domain into the frequency-domain wherein hydraulic pressure can be graphically plotted as a function of frequency and changes in hydraulic pressure as a function of frequency can be monitored over time as mixing progress, concrete stiffens, or materials such as water or chemical admixtures are added into the drum. Hence, the amplitude or height of the frequency peaks or curves represents the hydraulic pressure (in pounds per square inch, or psi) reflected as a function of frequency. The singular amplitude peak means that most of the hydraulic pressure required to rotate the empty drum occurs at primarily within a very narrow frequency bandwidth; this is consistent with the observation that the hydraulic pressure required to rotate an empty drum is fairly represented by a single sinusoidal curve, representing the lowest frequency, as suggested in FIG. 1.

In preferred embodiments of the invention, the hydraulic pressure waveform data (sequence of values corresponding to hydraulic pressure required to rotate the drum and cementitious material) is converted into the frequency-domain, such as by using FFT or DFT, so that the upper harmonic behavior of the drum contents can be analyzed further.

In further exemplary embodiments of the present invention, the height of the peaks can be assessed, as well as the width at the base of the peaks, and also including the total area of the peaks, as desired.

Figure 4:
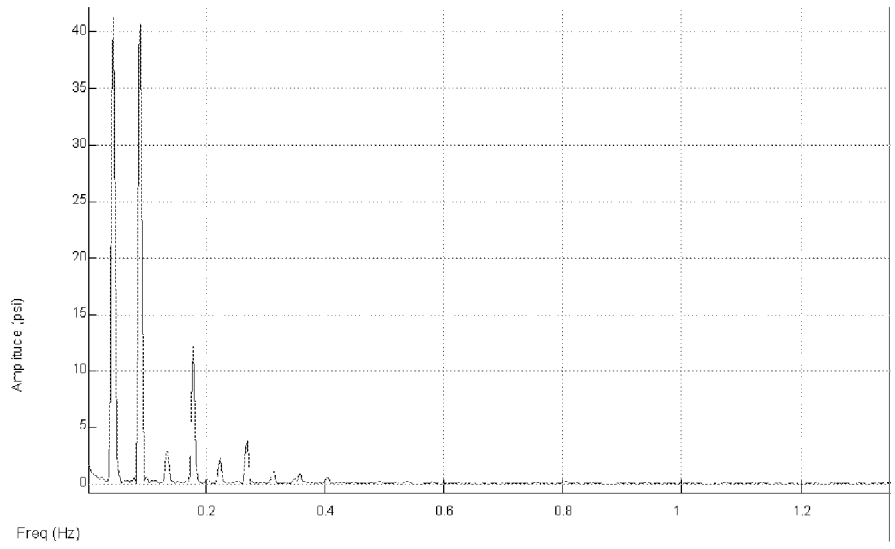
FIG. 4 is a graphic illustration of a frequency domain spectrum of the mixing drum loaded with concrete of FIG. 2 computed from Fast Fourier Transform (FFT) analysis.

FIG. 4 indicates what happens when concrete is loaded into the mixing drum, and the resultant hydraulic waveform is converted by Fast Fourier Transform (FFT) into the frequency-domain wherein frequency components are plotted as a function of frequency. While the waveform for the empty drum exhibits a peak amplitude at the frequency corresponding to the drum revolution rate, the hydraulic energy waveform of the concrete-loaded mixing drum demonstrates peak amplitudes at higher frequencies. This appearance of higher frequencies is believed to be generated by the mixing blades or paddles mounted on the inner wall surface of the mixing drum. A typical truck mixer drum includes two equal helical or spiral blades mounted opposite of each other on the inside of the drum. The measured waveform provided by FFT analysis is a summation of a frequency associated with the rotation of the drum itself and other frequencies associated with concrete being displaced or sheared by the blades. A second peak appearing at a higher frequency (to the right side of the first peak) represents a doubling of the frequency of the drum rotation. This phenomenon is believed to be caused by having two evenly-spaced-apart mixing blades, which are mounted on the inner wall of the rotating drum.

Figure 5:
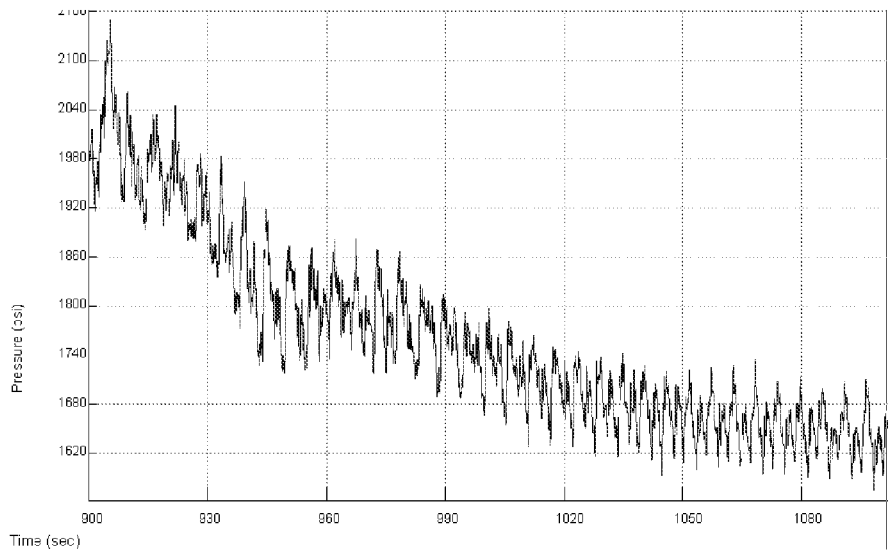
FIG. 5 is a graphic illustration of the hydraulic pressure over time (waveform) during mixing of a concrete batch.

FIG. 5 shows the hydraulic pressure waveform as batched concrete is mixed. Within this time-domain plot, the waveform is seen to change gradually over time during the mixing operation. Specifically, the time domain waveform changes from a predominantly sinusoidal curve with a single repeating peak to a curve with two peaks per rotation and with each peak a different height. The latter portion of the waveform is shaped as a "M" or "W" shape. Hence, exemplary methods and systems of the invention involve the analysis of the waveform properties of the data corresponding to "peaks" and "valleys" of the "M" or "W" shaped waveforms as graphically illustrated in FIG. 5. The appearance of the "M" or "W" shaped waveform is associated with a certain degree of mixing. In addition, the reduction in variation of the non-averaged hydraulic pressure (e.g. as measured by standard deviation over a certain time interval) and the decline and eventual stabilization of averaged hydraulic pressure are also associated with a certain degree of mixing. Therefore, these characteristics of the hydraulic pressure waveform can be analyzed and used to evaluate the mixing progress and ensure that concrete is fully mixed. It is important to confirm the properties of concrete after rather than before it is fully mixed. In addition, by knowing the extent of mixing, it is possible to estimate the final properties of the fully mixed concrete. The present inventors believe that the hydraulic pressure data after full mixing can be used for correlating with one or more physical properties of the cementitious material contained in the mixing drum, such as (a) load weight, (b) load volume, (c) concrete density, (d) concrete air content, (e) concrete slump, (f) concrete slump flow, (g) concrete flow table value, (h) concrete rheology (e.g., yield stress, viscosity, thixotropy), (i) segregation of concrete components, (j) concrete setting, (k) inclination of the mixing drum, (l) size and configuration of the internal drum structure; and (m) build-up of concrete in the drum. Such physical properties or information on the mixing drum itself could be stored in a data memory location, displayed graphically on a monitor, or printed on paper.

For example, in FIG. 5, between 900-930 seconds, the variations between the topmost peak and bottommost valley (or bottom of the wave) are much larger than those appearing between, for example, 1020-1080 seconds, suggesting that the concrete has not yet obtained uniformity at 900 seconds. Thus, once the variation between peaks decreases, such as suggested by the graph at 1020-1080 seconds, the "M" or "W" shape of the waveform is evident, and the average hydraulic pressure is stabilized, the mixing drum system can indicate that mixing is complete and can be programmed to calculate concrete quantity or properties, decrease rotational speed to conserve energy, allow discharge of fully mixed concrete, or make further additions of cementitious materials to adjust properties of the concrete.

In exemplary methods and systems of the invention, this information can be graphically displayed on a monitor, so that it is possible for the operator to start up the mixing of components at a certain time before pouring (at the delivery site), and the waveforms can be compared to stored waveforms so that the operator can visually ascertain when uniformity of the concrete mix has been attained. Alternatively, the waveform can be analyzed to determine the status of mixing (e.g. partially mix, fully mixed, or estimated time to fully mixed concrete) and this status can be graphically displayed on a monitor so that the operator can visually ascertain when uniformity of the concrete mix has been obtained.

The present inventors believe that waveform patterns in the sequence of hydraulic pressure data can be correlated with one or more cementitious material parameters, and verified either visually on monitor or by programming a computer processor to compare stored data with data obtained during the concrete delivery and/or pouring process.

For example, a known load weight may be correlated with a particular peak height at a given time and stored in computer-accessible memory location, such that for subsequent concrete loads having the same components, formulation, and rotation speed, the load weight can be automatically detected as a function of peak amplitude. A peak of the same height as previously recorded would mean the concrete load had the same weight (when registered by the pressure sensor at the same time and drum rotation speed); while a peak that was half the height could signify that the load was of certain lesser weight.

Similarly, the present inventors believe that other parts of the waveform shape, or certain patterns of the waveform shapes over time, can be used to analyze other parameters (or physical characteristics) of the cementitious material, such as slump and slump flow. For example, a concrete having a low slump would be expected to require more energy for turning the drum and would be less susceptible to flowing over the fins mounted within the drum, such that the shape of the waveform when transitioning between a higher peak and a lower valley within one rotational cycle of the mixing drum would be accompanied by a lot of "spiky" energy activity. This is clearly seen when comparing the shape of the waveforms in the range of 900-930 seconds with the shape of the waveforms in the range of 1050-1080 seconds, as illustrated graphically in FIG. 5. The waveforms seen in the range of 900-930 demonstrate a large degree of oscillation, suggesting that the concrete flowed less over the rotating mixing blades; whereas the smoother transition between peak amplitude and valleys suggests that the concrete flowed relatively more easily over the rotating mixing blades in the range of 1050-1080 seconds.

On the other hand, when the sequence of hydraulic energy values are converted into the frequency-domain using FFT, other valuable information begins to appear.

Figure 6:
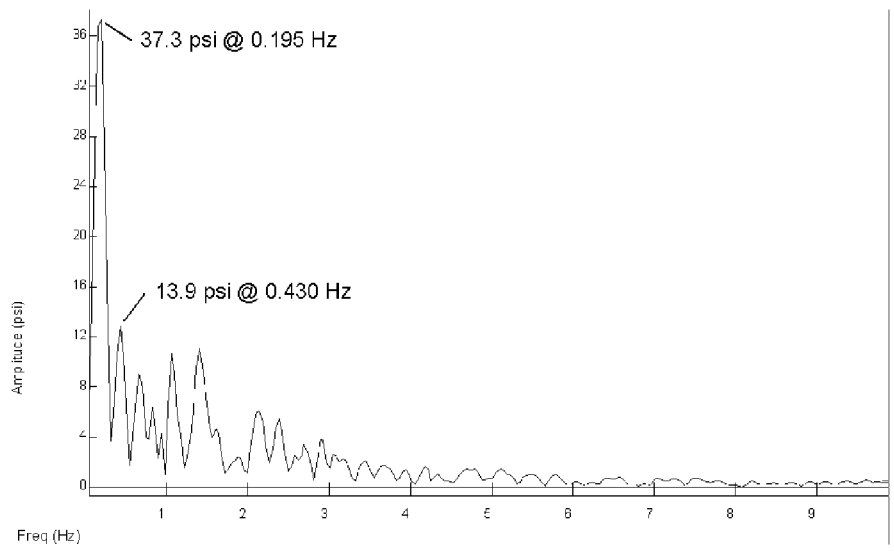
FIG. 6 is a graphic illustration of amplitude over frequency calculated using FFT analysis for partially-mixed concrete of FIG. 5.
Figure 7:
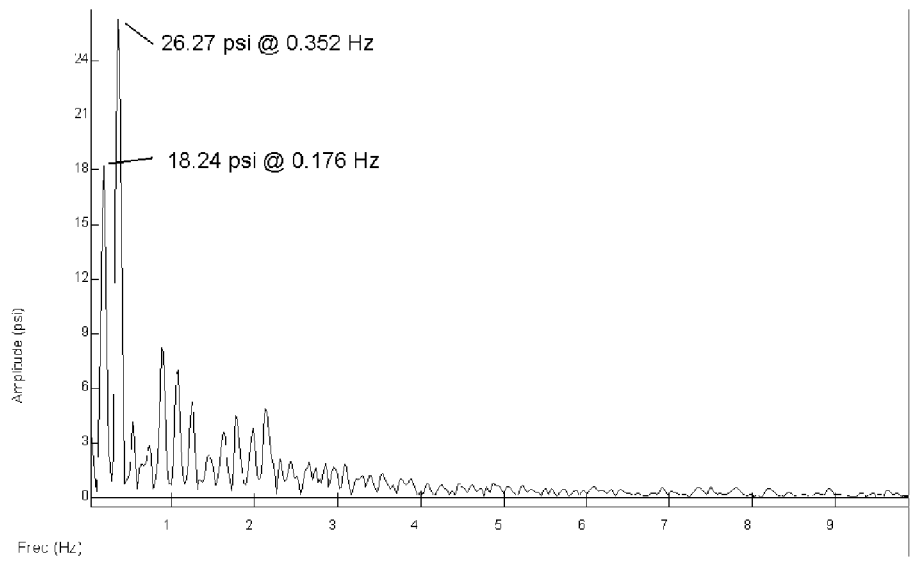
FIG. 7 is a graphic illustration of amplitude over frequency calculated using FFT analysis on a fully mixed concrete batch of FIG. 5.

FIG. 6 is a graphic plot in the frequency-domain after the hydraulic energy values are converted using FFT into the frequency domain wherein the first peak with frequency of 0.156 Hz and a second peak with frequency of 0.430 Hz both appear. Over time as mixing progresses, FIG. 7 indicates the amplitude of the first peak decreases and the amplitude of the second peak increases. The present inventors believe that this amplitude and phase change of different harmonics and sub-harmonics may be used to monitor the effect of different physical properties of the cementitious mix in the rotating drum. In this case, the partially mixed concrete is a stiff, granular material that does not flow over the blades inside the mixer. As mixing progresses and the batched ingredients in the mixer homogenize and transition from a granular bulk material to a fluid bulk material, the concrete starts to flow over the blades inside the mixer. The action of the fluid concrete flowing over the blades is believed by the inventors to be associated with the appearance of the peak amplitudes at different frequencies. In addition, the frequencies associated with each peak become harmonics or sub-harmonics—that is, each is a multiple of another. Therefore, the appearance and stabilization of this second peak at a different frequency is associated with the progress of mixing.

Figure 8:
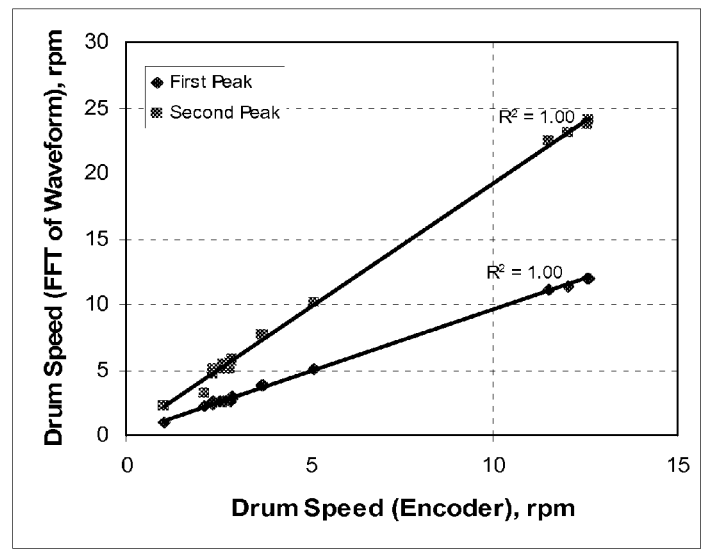
FIG. 8 is a graphic illustration of the relationship between actual rotating drum speed, measured using an encoder, and the drum speed calculated using FFT analysis of hydraulic pressure waveform.

FIG. 8 indicates the relationship between the actual drum speed, measured with an encoder, and the drum speed calculated based on FFT analysis of the hydraulic pressure waveform. The frequency associated with the first amplitude peak determined from the FFT, when converted from Hz to revolutions per minute, was equal to the drum speed. The frequency associated with the second amplitude peak was equal to twice the drum speed. The frequency associated with the second amplitude peak is twice the drum speed because it is believed to be associated with concrete acting on the blades in the drum. The presence of two blades in the drum results in a frequency associated with two times the drum speed. The use of FFT data obviates the need for the encoder.

The Fast Fourier Transform is an algorithm that permits computation of the Discrete Fourier Transform, which converts time domain data into frequency domain data. In fact, there are multiple FFT algorithms available. FFT can be used to report frequency, amplitude, phase, power spectrum, and power spectrum density or real and imaginary components.

The principles, preferred embodiments, and modes of operation of the present invention have been described in the foregoing specification. The invention which is intended to be protected herein, however, is not to be construed as limited to the particular forms disclosed, since these are to be regarded as illustrative rather than restrictive. Skilled artisans can make variations and changes without departing from the spirit of the invention.

It is claimed:

1. A mixing system comprising:
a mixing drum having an inner drum wall and at least two mixing blades mounted on the inner drum wall for mixing a provided concrete contained within the mixing drum;
a drive means for rotating the mixing drum containing the provided concrete at constant speed $S^{C1}$ in the range of 1-25 revolutions per minute;
a sensor for providing a sequence of values over time corresponding to the energy required by the drive means to rotate the mixing drum, the provided sequence of values enabling a computer processing unit to detect shape transitioning in the waveform data corresponding to concrete flowing over the at least two blades mounted in the drum within one rotational cycle of the mixing drum;
a data memory storage location having waveform data derived from a previously stored sequence of values over time corresponding to the energy required to rotate a mixing drum containing a previous concrete as monitored by a sensor during rotation of the mixing drum at a frequency of at least 10 times constant speed $S^{C1}$ of mixing drum rotation, the stored waveform data enabling a computer processing unit to detect shape transitioning in the waveform data corresponding to concrete flowing over the at least two blades mounted in the drum within one rotational cycle of the mixing drum; and
a computer processing unit which performs the following functions:
monitors at a frequency of at least 10 times constant speed $S^{C1}$ of mixing drum rotation the sequence of values provided by the energy sensor to obtain waveform data containing shape transitioning in waveform data corresponding to concrete flowing over at least two blades mounted in the drum within one rotational cycle of the mixing drum rotation, and corresponding to the amount of energy required by the drive means to rotate the mixing drum containing the provided concrete;
analyzes the provided sequence of values in the time domain, the frequency domain, or in both the time domain and frequency domain, for variations in waveform data within one rotational cycle of the mixing drum;
compares waveform data variations within the provided sequence of values to waveform data variations within the previously stored sequence of values; and
adjusts the slump, slump flow, or other property of the provided concrete by introducing a liquid into the mixing drum containing the provided concrete based on the comparison of compared waveform data variations in provided and previously stored sequences of values;
the waveform data variations being correlated with at least two properties or conditions of the concrete or mixing drum selected from (a) load weight, (b) load volume, (c) concrete density, (d) concrete air content, (e) concrete slump, (f) concrete slump flow, (g) concrete flow table value, (h) concrete rheology selected from yield stress, viscosity, and thixotropy, (i) segregation of concrete components, (j) concrete setting, (k) inclination of the mixing drum, (I) size and configuration of the internal drum structure; and (m) build-up of concrete in the drum.

2. The mixing system of claim 1 wherein the properties of the concrete are concrete air content and concrete slump.

3. The mixing system of claim 1 wherein the computer processing unit further compares the waveform data variations which were derived from provided and previously stored sequences of values and correlated with concrete slump flow.

4. The mixing system of claim 1 wherein a sequence of values and waveform data variations therein is displayed graphically on a visual display or chart.

5. The mixing system of claim 1 wherein the system provides a sequence of values and waveform data variations therein as a waveform pattern and the waveform is correlated to at least one of the parameters and the sequence of values and variations therein are analyzed as waveform patterns stored in a computer-accessible memory location, displayed on a monitor, printed on paper, or a combination thereof.

6. The mixing system of claim 1 wherein the liquid is water, at least one chemical admixture, or a mixture thereof.

7. The mixing system of claim 1 wherein the drive means is a hydraulic drive, and the sequence of values sensed by the sensor and analyzed by the computer processing unit corresponds to hydraulic pressure require to rotate the mixing drum.

8. The mixing system of claim 1 wherein the determination, storing, and reporting of mixing progress involves the computer processing unit comparing the provided sequence of values with the previously stored sequence of values, and the comparison involves values corresponding to features of "M" or "W" shaped time-domain waveform, waveform data variations in non-averaged hydraulic pressure, stabilization of averaged hydraulic pressure, or a combination thereof when hydraulic pressure data, corresponding to the energy required to rotate the mixing drum containing concrete, is graphically depicted as a function of time or frequency.

9. The mixing system of claim 1 wherein the waveform data variations compared by the computer processing unit comprise changes in peak amplitude and phase shift in the frequency domain.

10. A mixing system comprising:
a mixing drum having an inner drum wall and at least two mixing blades mounted on the inner drum wall for mixing a provided concrete contained within the mixing drum;
a drive means for rotating the mixing drum containing the provided concrete at constant speed $S^{C1}$ in the range of 1-25 revolutions per minute;
a sensor for providing a sequence of values over time corresponding to the energy required by the drive means to rotate the mixing drum, the provided sequence of values enabling a computer processing unit to detect shape transitioning in the waveform data corresponding to concrete flowing over the at least two blades mounted in the drum within one rotational cycle of the mixing drum;
a data memory storage location having waveform data derived from a previously stored sequence of values over time corresponding to the energy required to rotate a mixing drum containing a previous concrete as monitored by a sensor during rotation of the mixing drum at a frequency of at least 10 times constant speed $S^{C1}$ of mixing drum rotation, the stored waveform data enabling a computer processing unit to detect shape transitioning in the waveform data corresponding to concrete flowing over the at least two blades mounted in the drum within one rotational cycle of the mixing drum; and
a computer processing unit which performs the following functions:
monitors at a frequency of at least 10 times constant speed $S^{C1}$ of mixing drum rotation the sequence of values provided by the energy sensor to obtain waveform data containing shape transitioning in waveform data corresponding to concrete flowing over at least two blades mounted in the drum within one rotational cycle of the mixing drum rotation, and corresponding to the amount of energy required by the drive means to rotate the mixing drum containing the provided concrete;
analyzes the provided sequence of values in the time domain, the frequency domain, or in both the time domain and frequency domain, for variations in waveform data within one rotational cycle of the mixing drum;
compares waveform data variations within the waveform data provided by the sensed sequence of values to waveform data variations within the previously stored sequence of values; and
adjusts the slump, slump flow, or other property of the provided concrete by introducing a liquid into the mixing drum containing the provided concrete based on the comparison of waveform data variations in provided and previously stored sequences of values.

11. The mixing system of claim 10 wherein the waveform data variations are correlated with at least one property or condition of the concrete or mixing drum selected from (a) load weight, (b) load volume, (c) concrete density, (d) concrete air content, (e) concrete slump, (f) concrete slump flow, (g) concrete flow table value, (h) concrete rheology selected from yield stress, viscosity, and thixotropy, (i) segregation of concrete components, (j) concrete setting, (k) inclination of the mixing drum, (l) size and configuration of the internal drum structure; and (m) build-up of concrete in the drum.

12. The mixing system of claim 11 wherein the waveform data variations are correlated with concrete air content and concrete slump.

13. The mixing system of claim 10 wherein the computer processing unit further compares the calculated variations which were derived from provided and previously stored sequences of values corresponding with concrete slump flow.

14. The mixing system of claim 10 wherein a sequence of values and calculated variations therein is displayed graphically on a visual display or chart as a waveform.

15. The mixing system of claim 10 wherein the system provides a sequence of values and calculated variations therein as a waveform pattern and the waveform is correlated to at least one of the parameters and the sequence of values and variations therein are analyzed as waveform patterns stored in a computer accessible memory location, displayed on a monitor, printed on paper, or a combination thereof.

16. The mixing system of claim 10 wherein the liquid is water, at least one chemical admixture, or a mixture thereof.

17. The mixing system of claim 10 wherein the determination, storing, and reporting of mixing progress involves the computer processing unit comparing the provided sequence of values with the previously stored sequence of values, and the comparison involves values corresponding to features of "M" or "W" shaped time-domain waveform, calculated variations in non-averaged hydraulic pressure, stabilization of averaged hydraulic pressure, or a combination thereof when hydraulic pressure data, corresponding to the energy required to rotate the mixing drum containing concrete, is graphically depicted as a function of time or frequency.

18. The mixing system of claim 10 wherein the drive means is a hydraulic drive.

19. The mixing system of claim 10 wherein the calculated variations compared by the computer processing unit comprise changes in peak amplitude and phase shift in the frequency domain.

* * * * *